United States Patent
Hashimoto (10) Patent No.: US 10,628,941 B2
(45) Date of Patent: Apr. 21, 2020

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Takayuki Hashimoto, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 196 days.

(21) Appl. No.: 15/946,141

(22) Filed: Apr. 5, 2018

(65) Prior Publication Data

US 2018/0293729 A1 Oct. 11, 2018

(30) Foreign Application Priority Data

Apr. 10, 2017 (JP) .................................. 2017-077256

(51) Int. Cl.
| | |
|---|---|
| *G06T 7/00* | (2017.01) |
| *G06K 9/62* | (2006.01) |
| *G06K 9/46* | (2006.01) |
| *A61B 6/00* | (2006.01) |
| *A61B 6/03* | (2006.01) |

(52) U.S. Cl.
CPC .............. *G06T 7/0012* (2013.01); *A61B 6/03* (2013.01); *A61B 6/5217* (2013.01); *G06K 9/4628* (2013.01); *G06K 9/6267* (2013.01); *G06K 9/6271* (2013.01); *A61B 6/463* (2013.01); *G06K 2209/051* (2013.01); *G06T 2207/10072* (2013.01); *G06T 2207/20081* (2013.01); *G06T 2207/30061* (2013.01); *G06T 2207/30096* (2013.01)

(58) Field of Classification Search
CPC . G06T 7/0012; G06T 7/10; G06T 7/11; G06T 7/174; G06T 2207/30096; G06K 9/6267; G06K 2209/051; A61B 6/5217
See application file for complete search history.

(56) References Cited

U.S. PATENT DOCUMENTS

| 2015/0117737 A1 | 4/2015 | Kim et al. ............ G06T 7/0012 |
| 2015/0133784 A1* | 5/2015 | Kapoor et al. ......... A61B 8/483 |
| | | 600/438 |

FOREIGN PATENT DOCUMENTS

JP 2015-80720 A 4/2015

* cited by examiner

*Primary Examiner* — Andrew W Johns
(74) *Attorney, Agent, or Firm* — Birch, Stewart, Kolasch & Birch, LLP (57) ABSTRACT

The image processing apparatus includes: a sectional image acquisition unit that acquires a plurality of sectional images in a plurality of sectional directions of a test subject; a primary classification unit that performs a primary classification process of specifying, with respect to each of the plurality of sectional images, the type of a tissue or a lesion to which each pixel of each sectional image belongs; a secondary classification unit that performs a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs; and a correction unit that corrects a result of the secondary classification process on the basis of an anatomic feature of the tissue or the lesion, or an image feature value thereof.

11 Claims, 5 Drawing Sheets

IMAGE PROCESSING APPARATUS, IMAGE PROCESSING METHOD, AND IMAGE PROCESSING PROGRAM

CROSS-REFERENCE TO RELATED APPLICATION

This application claims priority from Japanese Patent Application No. 2017-077256, filed on Apr. 10, 2017, the disclosure of which is incorporated by reference herein in its entirety.

BACKGROUND

Field of the Invention

The present invention relates to an image processing apparatus, an image processing method, and an image processing program that classify types of tissues or lesions included in a sectional image.

Related Art

In recent years, according to advances in medical equipment such as a computed tomography apparatus (CT) or a magnetic resonance imaging (MRI) apparatus, a high-quality and high-resolution three-dimensional image has been used in image diagnosis.

In this regard, interstitial pneumonia is known as a pulmonary diseases. A method for analyzing a sectional image of a patient having interstitial pneumonia to classify and quantize lesions showing a specific symptom such as a honeycomb lung, a reticular shadow or a cyst included in a sectional image has been proposed. In this way, by analyzing the sectional image to classify and quantize the lesion, it is possible to easily determine the degree of the pulmonary disease. Further, by allocating different colors to regions that are classified and quantized in this way, it is possible to easily diagnose how much of a specific symptom region is included in the image.

However, in a technique in the related art, since classification is performed with respect to a two-dimensional sectional image, there is a case where the classification is performed as regions that are discontinuous in a depth direction of the two-dimensional sectional image, which is not appropriate classification in terms of anatomy.

JP2015-80720A discloses a method for creating a plurality of two-dimensional images from a three-dimensional image and evaluating and determining a lesion with respect to each of the plurality of two-dimensional images in order to determine whether the lesion is benign or malignant. However, JP2015-80720A discloses only the method for classifying whether the lesion included in the two-dimensional image is benign or malignant, and does not disclose a method for appropriately classifying lesion regions.

SUMMARY

In consideration of the above-mentioned problems, an object of the invention is to provide an image processing apparatus, an image processing method, and an image processing program capable of classifying, in a case where tissues or lesions included in a sectional image are classified using the sectional image, regions of the tissues or the lesions with high accuracy.

According to an aspect of the invention, there is provided an image processing apparatus comprising: a sectional image acquisition unit that acquires a plurality of sectional images in a plurality of different sectional directions of a test subject; a primary classification unit that performs a primary classification process of specifying, with respect to each of the plurality of sectional images, the type of a tissue or a lesion to which each pixel of each sectional image belongs; a secondary classification unit that performs a secondary classification process of evaluating a result of the primary classification process with respect to each sectional image, with respect to a pixel that is common to the plurality of sectional images, to re-specify the type of a tissue or a lesion to which the pixel that is common to the plurality of sectional images belongs; and a correction unit that corrects a result of the secondary classification process on the basis of an anatomic feature of the tissue or the lesion, or an image feature value thereof.

In the image processing apparatus according to this aspect of the invention, the correction unit may correct the result of the secondary classification process with respect to each pixel using a sectional image in a specific sectional direction.

In the image processing apparatus according to this aspect of the invention, it is preferable that the specific sectional direction is a slicing direction in imaging of the test subject.

In the image processing apparatus according to this aspect of the invention, it is preferable that the sectional image in the specific sectional direction is a sectional image with the highest resolution among the sectional images in the plurality of sectional directions.

In the image processing apparatus according to this aspect of the invention, the correction unit may correct the result of the secondary classification process on the basis of a signal value of each pixel of the sectional image in the specific sectional direction.

In the image processing apparatus according to this aspect of the invention, the correction unit may correct the result of the secondary classification process on the basis of an anatomic feature of the shape or the position of the tissue or the lesion.

In the image processing apparatus according to this aspect of the invention, the correction unit may correct, in a case where there is an abnormality in continuity in a three-dimensional space of an edge or a centroid position of a tissue or a lesion specified by each pixel classified by the secondary classification process, the result of the secondary classification process with respect to each pixel.

In the image processing apparatus according to this aspect of the invention, in a case where the secondary classification unit performs the second classification process, the secondary classification unit may add a weight based on each resolution of each of the sectional images to the result of the primary classification process with respect to each sectional image for the evaluation.

In the image processing apparatus according to this aspect of the invention, the primary classification unit may perform the primary classification process using a discriminator generated through machine learning.

According to another aspect of the invention, there is provided an image processing method comprising: acquiring a plurality of sectional images in a plurality of different sectional directions of a test subject; performing a primary classification process of specifying, with respect to each of the plurality, of sectional images, the type of a tissue or a lesion to which each pixel of each sectional image belongs; performing a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs; and correcting a result of the secondary classification process on the basis of an anatomic feature of the tissue or the lesion, or an image feature value thereof.

According to still another aspect of the invention, there is provided an image processing program that causes a computer to function as: a sectional image acquisition unit that acquires a plurality of sectional images in a plurality of different sectional directions of a test subject; a primary classification unit that performs a primary classification process of specifying, with respect to each of the plurality of sectional images, the type of a tissue or a lesion to which each pixel of each sectional image belongs; a secondary classification unit that performs a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs; and a correction unit that corrects a result of the secondary classification process on the basis of an anatomic feature of the tissue or the lesion, or an image feature value thereof.

According to still another aspect of the invention, there is provided an image processing apparatus comprising: a memory that stores a command to be executed in a computer; and a processor configured to execute the stored command, in which the processor executes a process of acquiring a plurality of sectional images in a plurality of different sectional directions of a test subject; a primary classification process of specifying, with respect to each of the plurality of sectional images, the type of a tissue or a lesion to which each pixel of each sectional image belongs; a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs; and a process of correcting a result of the secondary classification process on the basis of an anatomic feature of the tissue or the lesion, or an image feature value thereof.

According to the image processing apparatus, the image processing method, and the image processing program according to the invention, a plurality of sectional images in a plurality of different sectional directions of a test subject are acquired; and a primary classification process of specifying, with respect to each of the plurality of sectional images, the type of a tissue or a lesion to which each pixel of each sectional image belongs is performed. Then, a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs is performed. In this way, by performing the secondary classification process, it is possible to obtain a classification result in further consideration of a depth direction of sectional images.

Further, according to the image processing apparatus, the image processing method, and the image processing program according to the invention, since the result of the secondary classification process is corrected on the basis of an anatomic feature of a tissue or a lesion, or an image feature value thereof, it is possible to achieve a classification result based on an anatomic structure, and to classify a region of the tissue or the lesion with high accuracy.

DETAILED DESCRIPTION

Figure 1:
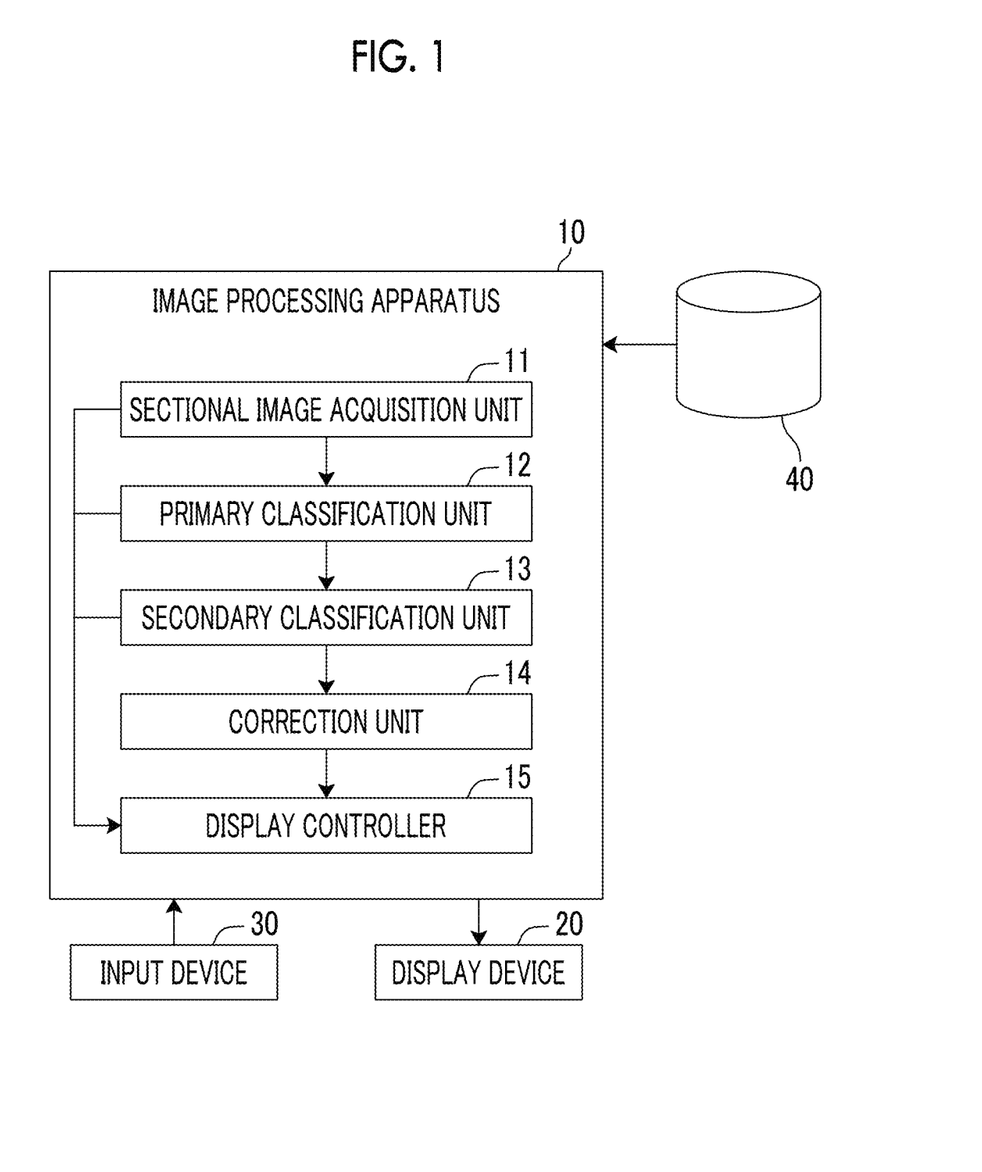
FIG. 1 is a block diagram showing a schematic configuration of a medical image diagnosis support system using an embodiment of an image processing apparatus according to the invention.

Hereinafter, a medical image diagnosis support system using an embodiment of an image processing apparatus, an image processing method, and an image processing program of the invention will be described in detail with reference to the accompanying drawings. FIG. 1 is a block diagram showing a schematic configuration of a medical image diagnosis support system according to an embodiment.

The medical image diagnosis support system according to this embodiment includes an image processing apparatus 10, a display device 20, an input device 30, and a three-dimensional image storage server 40, as shown in FIG. 1.

The image processing apparatus 10 is configured by installing an image processing program according to the embodiment into a computer. The image processing program may be recorded on a recording medium such as a digital versatile disc (DVD) or a compact disc read-only memory (CD-ROM) for distribution, and may be installed into the computer from the recording medium. Alternatively, the image processing program may be stored in a storage device of a server computer connected to a network or a network storage in a state of being accessible from the outside, and may be downloaded and installed into a computer to be used by a doctor as necessary.

The image processing apparatus 10 includes a central processing unit (CPU), and a storage device such as a semiconductor memory, a hard disk or a solid-state drive (SSD), and the like, and through the hardware, a sectional image acquisition unit 11, a primary classification unit 12, a secondary classification unit 13, a correction unit 14, and a display controller 15 are configured, as shown in FIG. 1. Further, as the image processing program installed in the storage device is executed by the CPU, the respective units are operated, respectively. The image processing apparatus 10 is not configured using only a general-purpose CPU, but may be also configured using an application specific integrated circuit (ASIC), a field-programmable gate array (FPGA), or the like for a specific usage.

The sectional image acquisition unit 11 acquires sectional images of a test subject that is imaged in advance before an operation, or before an inspection, for example. As the sectional images, sliced data output from a CT apparatus, a magnetic resonance imaging (MRI) apparatus, and the like, sliced data output from a multi slice (MS) CT apparatus and a cone beam CT apparatus, and the like may be used. The sectional images are stored in advance together with test subject identification information in the three-dimensional image storage server 40, and the sectional image acquisition unit 11 reads out and acquires sectional images corresponding to test subject identification information input through the input device 30 from the three-dimensional image storage server 40.

Figure 2A:
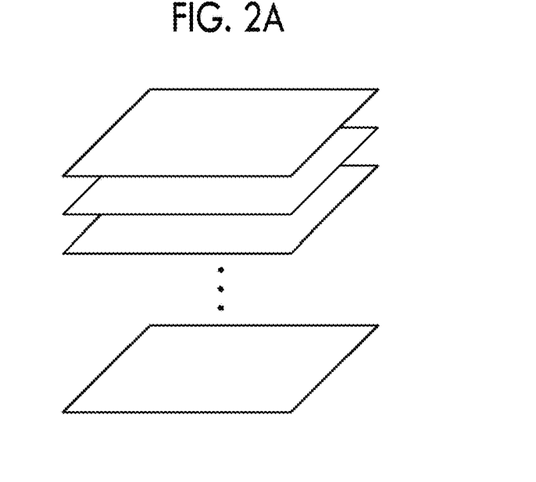
FIGS. 2A to 2C are diagrams showing examples of sectional images in a plurality of different sectional directions.
Figure 2B:
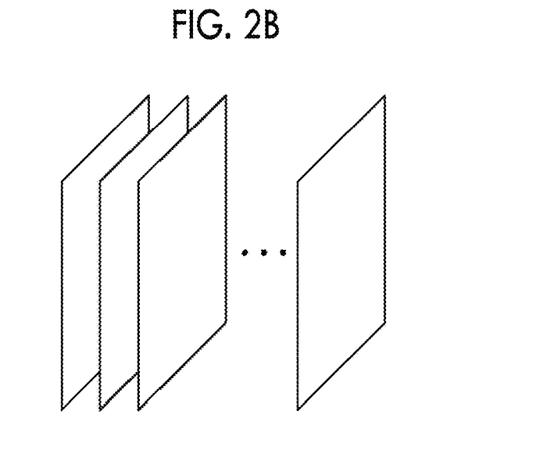
Figure 2C:
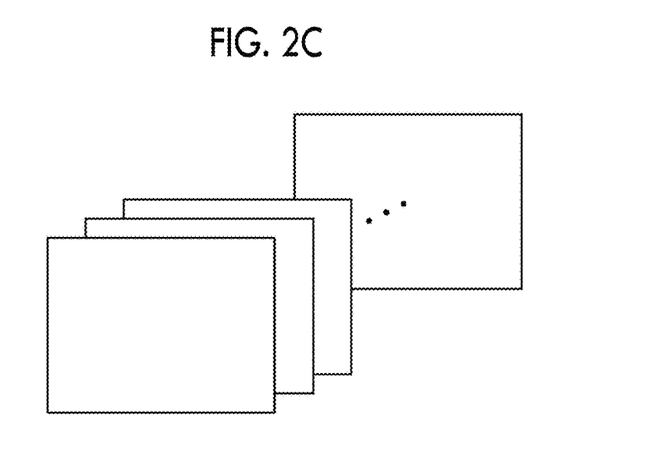

Further, the sectional image acquisition unit 11 acquires sectional images in a plurality of different sectional directions of a test subject. As the sectional directions, an axial direction, a sagittal direction, a coronal direction, an oblique direction, and the like may be used. It is preferable that the sectional image acquisition unit 11 acquires at least three sectional images. The sectional image acquisition unit 11 acquires a plurality of sectional images with respect to each of three different sectional directions as shown in FIGS. 2A to 2C.

In a case where sectional images in a plurality of difference sectional directions of a test subject are stored in the three-dimensional image storage server 40 in advance, the sectional image acquisition unit 11 acquires the plurality of sectional images, but in a case where volume data on the test subject is stored in the three-dimensional image storage server 40, the sectional image acquisition unit 11 may read out the volume data, and may generate and acquire sectional images in a plurality of different sectional directions from the volume data.

The primary classification unit 12 performs a primary classification process of specifying the type of a tissue or a lesion to which each pixel of each sectional image belongs, with respect to each of the plurality of sectional images acquired by the sectional image acquisition unit 11. In this embodiment, a plurality of sectional images including a lung region are acquired by the sectional image acquisition unit 11, and the type of a tissue or a lesion to which each pixel of each sectional image belongs is specified. Hereinafter, only a primary classification process with respect to one sectional image in the axial direction among the plurality of sectional images will be described, but it is assumed that the primary classification process is similarly performed with respect to sectional images in other sectional directions.

The primary classification unit 12 according to this embodiment includes a discriminator configured of a multilayered neural network generated by deep learning that is machine learning, and specifies the type of a tissue or a lesion to which each pixel of each sectional image belongs, using the discriminator.

In the multilayered neural network, a computational process is performed in each layer using various kernels with respect to data on a plurality of different feature values obtained through a previous-stage layer. Then, by further performing a computational process in a next-stage layer and subsequent layers with respect to the data on the feature values obtained by the former computational process, it is possible to improve a recognition rate of the feature values and to classify the input data into a plurality of classes.

Figure 3:
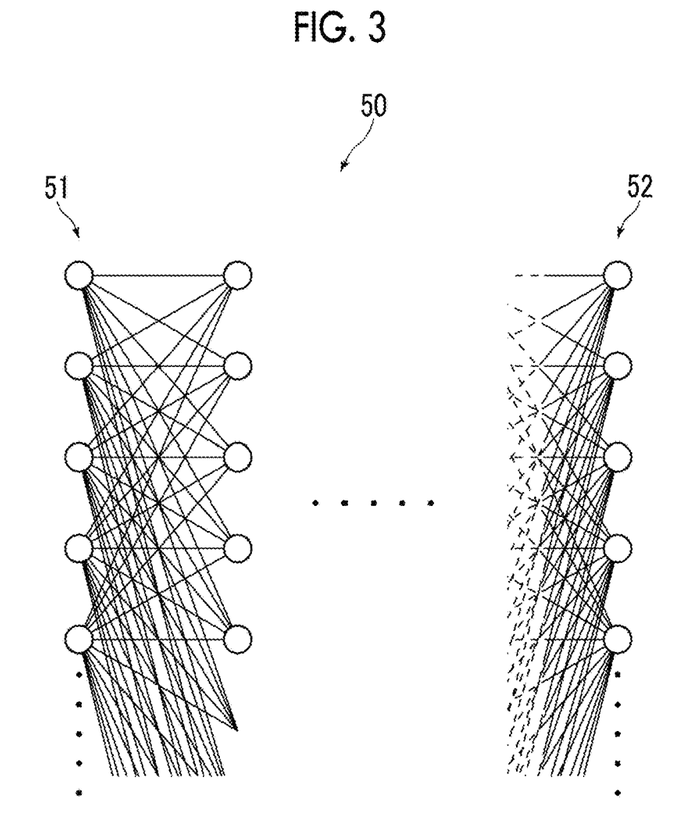
FIG. 3 is a diagram showing an example of a multilayered neural network.

FIG. 3 is a diagram showing an example of such a multilayered neural network. As shown in FIG. 3, a multi-layered neural network 50 includes a plurality of layers including an input layer 51 and an output layer 52. In this embodiment, learning is performed so that a lung region included in a sectional image is classified into a frosted glass shadow, a normal shadow, a bronchial tube, a honeycomb lung, a reticular shadow, a consolidation region, a low absorption region, and a cyst.

In this embodiment, the learning is performed with respect to these eight types of lung regions using millions of multiple pieces of teacher data in the multilayered neural network 50. In the learning, a region-of-interest of a predetermined size (for example, 1.5 cm×1.5 cm) is cut from a sectional image of which the type of a tissue or a lesion is already known, and the region-of-interest is used as teacher data. Further, the teacher data is input to the multilayered neural network 50, and a classification result of the type of the tissue or the lesion is output therefrom. Then, the output result is compared with the teacher data, and according to whether its answer is correct or incorrect, coupling weights, between respective layers, of units (indicated by circles in FIG. 3) included in each layer of the multilayered neural network 50 are corrected toward an input side from an output side. The correction of the coupling weights is repeated by a predetermined number of times or until a correct answer rate of the output classification result reaches 100% using the multiple pieces of teacher data, and then, the learning is terminated.

Further, in a case where the primary classification process is performed using the discriminator that includes the above-described multilayered neural network 50, the primary classification unit 12 sequentially cuts a region-of-interest having the same size as that of the teacher data from sectional images to be classified, and inputs the region-of-interest to the discriminator that includes the multilayered neural network 50. Thus, with respect to a central pixel of the cut region-of-interest, an evaluation value corresponding to each of the eight types of classifications is output. The evaluation value corresponding to each classification is an evaluation value indicating a possibility that the central pixel belongs to each classification. As the evaluation value is larger, the possibility that the central pixel belongs to the classification is higher. In addition, the discriminator classifies the central pixel of the region-of-interest into a tissue or a lesion with the largest evaluation value, among the eight types of tissues or lesions. Thus, every pixel in the lung region included in the sectional image is classified into any one of eight types of tissues or lesions.

The primary classification unit 12 similarly performs the primary classification process with respect to sectional images in other sectional directions, instead of the sectional image in the axial direction as described above, so that each pixel in each sectional image is classified into any one of eight types of tissues or lesions.

Next, the secondary classification unit 13 will be described. The secondary classification unit 13 evaluates results of the primary classification process with respect to each of the plurality of sectional images, with respect to a pixel that is common to the plurality of sectional images used in the primary classification unit 12, to re-specify the type of a tissue or a lesion to which the pixel that is common to the plurality of sectional images belongs.

Figure 4:
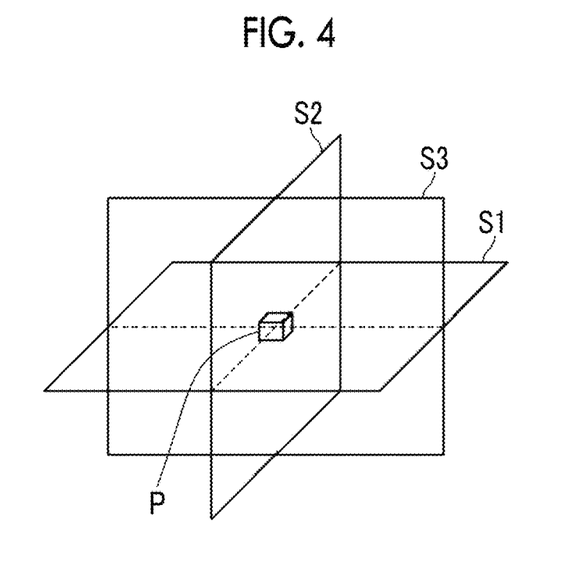
FIG. 4 is a diagram for illustrating a secondary classification process.

Specifically, as shown in FIG. 4, with respect to a pixel P that is common to three sectional images S1, S2, and S3, results of the primary classification process with respect to the sectional images S1, S2, and S3 are respectively acquired, the three results of the primary classification process are evaluated, and the type of a tissue or a lesion to which the pixel P belongs is specified.

As a method for evaluating the three results of the primary classification process, for example, a method for specifying, in a case where two or more same results are included in the three results of the primary classification process, the results may be specified as a final classification of the pixel P. That is, the results of the primary classification process of which the number is largest may be specified as the final classification of the pixel P.

Further, for example, as the result of the primary classification process, an evaluation value corresponding to each of eight types of classifications may be acquired. In this case, in the secondary classification process, with respect to the respective sectional images S1, S2, and S3, an evaluation value of the pixel P corresponding to each of the eight types of classifications is acquired, a classification corresponding to the largest evaluation value among 24 (the number (3) of sectional images×the number (8) of classifications) evaluation values may be specified as the final classification of the pixel P. In addition, an average value may be calculated for each classification with respect to the above-described 24 evaluation values, and a classification corresponding to the largest average value may be specified as the final classification of the pixel P.

Furthermore, as described above, in a case where the secondary classification process is performed using an evaluation value corresponding to each classification, a weight based on a resolution of each sectional image may be added to each evaluation value for evaluation. Specifically, for example, it is assumed that a relationship between a resolution R1 of the sectional image S1, a resolution R2 of the sectional image S2, and a resolution R3 of the sectional image S3 shown in FIG. 5 satisfies R1>R2>R3. In this case, it is preferable that a weight coefficient C1 added to an evaluation value of the pixel P of the sectional image S1 corresponding to each classification, a weight coefficient C2 added to an evaluation value of the pixel P of the sectional image S2 corresponding to each classification, and a weight coefficient C3 added to an evaluation value of the pixel P of the sectional image S3 corresponding to each classification are set to satisfy C1>C2>C3. By adding the weights in this way, it is possible to improve classification accuracy.

Further, in a case where the secondary classification process is performed using the evaluation value of the pixel P corresponding to each classification as described above, a weight may be added to the evaluation value corresponding to each classification in accordance with a position of the pixel P in a sectional image. Specifically, for example, a cyst and pleural effusion may be formed in a similar contour shape on a sectional image, and thus, there is a possibility that a pixel that belongs to the pleural effusion is misclassified as a pixel that belongs to the cyst. Thus, in a case where the pixel P is disposed in a lung region, a weight for increasing an evaluation value of the pixel P for the cyst may be added, and on the other hand, in a case where the pixel P is in a peripheral region other than the lung region, a weight for decreasing an evaluation value of the pixel P for the cyst may be added. The lung region in the sectional image may be extracted by threshold value processing, may be extracted using a region expansion method, or may be extracted using an arbitrary method.

In addition, a pixel that belongs to a honeycomb lung generally has a high signal value, but in a case where a bronchial wall is thick, a pixel around a bronchial tube also has a high signal value, and thus, there is a case where the pixel around the bronchial tube is misclassified as a pixel that belongs to the honeycomb lung. Accordingly, in a case where the pixel P is disposed around the bronchial tube, a weight for decreasing an evaluation value of the pixel P for the honeycomb lung and a weight for increasing an evaluation value thereof for the bronchial tube may be added. On the other hand, in a case where the pixel P is not around the bronchial tube, a weight for increasing an evaluation value of the pixel P for the honeycomb lung and a weight for decreasing an evaluation value thereof for the bronchial tube may be added. A region of the bronchial tube may be extracted using a separately known method. For example, a pixel inside the bronchial tube has a low pixel value since it corresponds to an air region, but the bronchial wall has a relatively high pixel value. Thus, the bronchial tube may be extracted by performing structure analysis of a shape based on a distribution of pixel values. For example, a method for using Hessian matrices may be used.

Further, in the above description, the secondary classification process with respect to one pixel P has been described, but with respect to all pixels on a three-dimensional space, the secondary classification process is performed on the basis of the result of the primary classification process in a similar way to the above description, so that the type of a tissue or lesion to which each pixel belongs is specified.

Then, the correction unit 14 will be described. The correction unit 14 corrects the result of the secondary classification process on the basis of an anatomic feature of the tissue or the lesion, or an image feature value thereof.

Here, even in a case where the tissue or the lesion to which each pixel belongs is specified by the above-described secondary classification unit 13, the classification result may be different from a result based on an anatomic structure.

Figure 5:
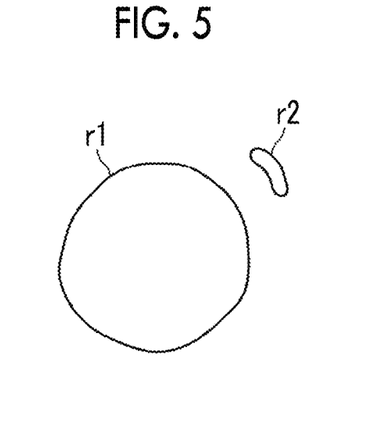
FIG. 5 is a diagram showing an example in which a cyst is misclassified.
Figure 6:
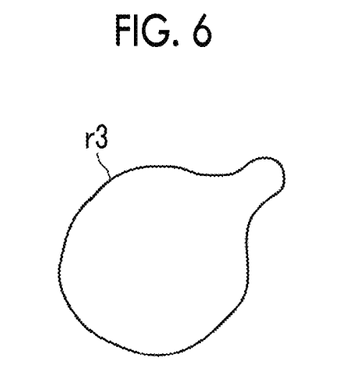
FIG. 6 is a diagram showing another example in which a cyst is misclassified.

Specifically, for example, a contour of a cyst forms a continuous smooth curve, but as a result of the secondary classification process, there is a case where a contour of a region that includes pixels classified as a cyst does not form a continuous smooth curve. For example, as shown in FIG. 5, there is a case where a region that includes pixels classified as a cyst becomes two divided regions r1 and r2. Further, as shown in FIG. 6, there is a case where there is an abnormality in an edge of a cyst region, such as a case where a protrusion is present on a contour of a region r3 that includes pixels classified as a cyst, or conversely, a case where a recess is present.

The correction unit 14 of this embodiment corrects the result of the secondary classification process to obtain a result based on an anatomic structure. Specifically, the correction unit 14 corrects the result of the secondary classification process with respect to each pixel using a sectional image in a specific sectional direction. As the sectional image in the specific sectional direction, a sectional image from which a tissue or a lesion can be extracted with higher accuracy is preferably used. For example, it is preferable that a sectional image in a sectional direction with the highest resolution among a plurality of sectional images used in a case where the primary classification process is performed is used.

Specifically, for example, a cyst region is extracted by performing a threshold value process or a filtering process using pixel values of the sectional image in the sectional direction with the highest resolution, and its contour is acquired as an image feature value. Further, correction is performed by matching a region that includes pixels classified as a cyst by the secondary classification process and the contour. Thus, it is possible to exclude the region r2 shown in FIG. 5 from the cyst region, and to remove the protrusion of the region r3 shown in FIG. 6. Further, in addition to the cyst, a bronchial region is extracted by performing a threshold value process, a filtering process, or the like using the pixel values of the sectional image, and its contour is acquired as an image feature value. In addition, correction may be performed by matching a region that includes pixels classified as a bronchial tube by the secondary classification process and the contour.

In the above description, the cyst region or the bronchial region is extracted, but it is not essential that a lesion or a tissue is specified. For example, a sectional image may be segmented by analyzing an edge or a shape included in the sectional image, and a region that includes pixels classified as a specific lesion or tissue by the secondary classification process may be widened or narrowed up to a segmented region.

Further, in a case where the correction is performed, signal values included in regions classified by the secondary classification process may be used as image feature values. Specifically, a distribution of the signal values included in the regions classified by the secondary classification process may be analyzed, and in a case where a high signal value region and a low signal value region are present, by separating the regions using a discriminant analysis method, a regions of signal values indicating a tissue such as the above-described cyst or bronchial tube may be determined for correction. For example, in a case where a sectional image is a CT image, since a signal value of an air region is close to $-1024$, but a tissue such as a bronchial wall or a blood vessel shows a signal value that is equal to or greater than 0, in a case where a region of a signal value close to an air region and a high signal value close to a blood vessel or the like are included in a cyst region classified by the secondary classification process, a region of a low signal value group among separated signal value groups is determined as a corrected cyst region.

Further, a threshold value process may be performed with respect to the signal value of the cyst region classified by the secondary classification process using a specific threshold value such as $-950$ that is a signal value in a low absorption band, and then, the correction may be performed.

In addition, the region classified by the secondary classification process or the region corrected by the above-described correction method may be expanded by one unit (1 voxel or 1 pixel) toward the outside of the region, and region portions of which distributions of signal values are close to each other may be widened, and then, the correction may be performed.

For example, in the case of a cyst region, a central region is an air region and has a low signal value, but an edge region is a partition of lung tissues or is a fibrotic tissue, and thus, has a high signal value. Accordingly, by expanding the region until the region reaches a region of a high signal value by one unit, the correction may be performed. Further, in a case where an edge (high signal value) region is detected in the cyst region classified by the secondary classification process so that the region is divided into regions, distributions (dispersions, standard deviations, or the like) of signal values in the divided regions may be calculated and compared with each other, and a region close to a lung field may be excluded, and then, the correction may be performed.

Further, in the above description, the correction is performed using an image feature value, but the invention is not limited thereto, and the correction may be performed using an anatomic feature of a tissue or a lesion. Specifically, as described above, there is a case where a cyst and pleural effusion are formed in a similar contour shape on a sectional image, and thus, there is a possibility that a pleural effusion region is misclassified as a cyst region. Thus, in a case where a region classified as a cyst is a peripheral region other than a lung region, the region may be considered as a pleural effusion region, and may be removed. That is, the correction may be performed on the basis of a feature of an anatomic position of the cyst. In addition, in a case where a region classified as a cyst corresponds to the regions r1 and r2 that are divided as shown in FIG. 5, the region r2 may be removed on the basis of a feature of such an anatomic shape that a contour of a cyst forms a continuous smooth curve. Further, in a case where a region classified as a cyst is a region having a protrusion as shown in FIG. 6, the protrusion portion may be removed on the basis of a feature of such an anatomic shape that the contour of the cyst is a continuous smooth curve.

In the above description, in a case where the correction is performed, a sectional image in a sectional direction with the highest resolution among a plurality of sectional images used in a case where the primary classification process is performed is used, but the invention is not limited thereto. For example, a sectional image in a slicing direction in imaging of a test subject may be used. The sectional image in the slicing direction in imaging refers to a so-called original image. For example, in a case where the slicing direction in imaging is a direction orthogonal to a body axis, a sectional image in an axial direction becomes the sectional image in the slicing direction. Since the sectional image in the slicing direction is an image with the highest resolution, it is possible to enhance classification accuracy.

Figure 7:
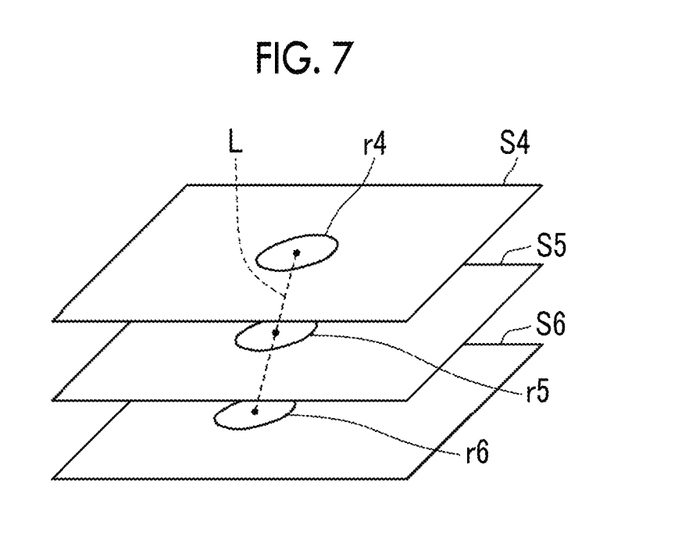
FIG. 7 is a diagram for illustrating continuity of a centroid position of each region classified as a cyst.

Further, the correction unit 14 may perform the above-described correction only in a case where an abnormality of an edge is detected in a process of detecting the abnormality of the edge such as a protrusion or a recess in a region classified as a cyst as shown in FIG. 6. In addition, in a case where sectional images S4, S5, and S6 for which the secondary classification process is performed are disposed in parallel on a three-dimensional space as shown in FIG. 7, and for example, in a case where an abnormality in continuity of centroid positions of respective regions r4, r5, and r6 classified as cysts in the respective sectional images S4, S5, and S6 is detected, the above-described correction may be performed with respect to the regions classified as the cysts in the respective sectional images S4, S5, and S6. With respect to the abnormality in the continuity of the centroid positions, for example, a linearity of a line L that connects the centroid positions may be evaluated, and in a case where the linearity is equal to or smaller than a predetermined threshold value, it may be recognized that there is an abnormality in continuity of centroid positions.

Returning to FIG. 1, the display controller 15 allocates a color to each classified region on the basis of the result of the secondary classification process corrected by the correction unit 14 to generate a mapping image, and displays the mapping image on the display device 20.

Figure 8:
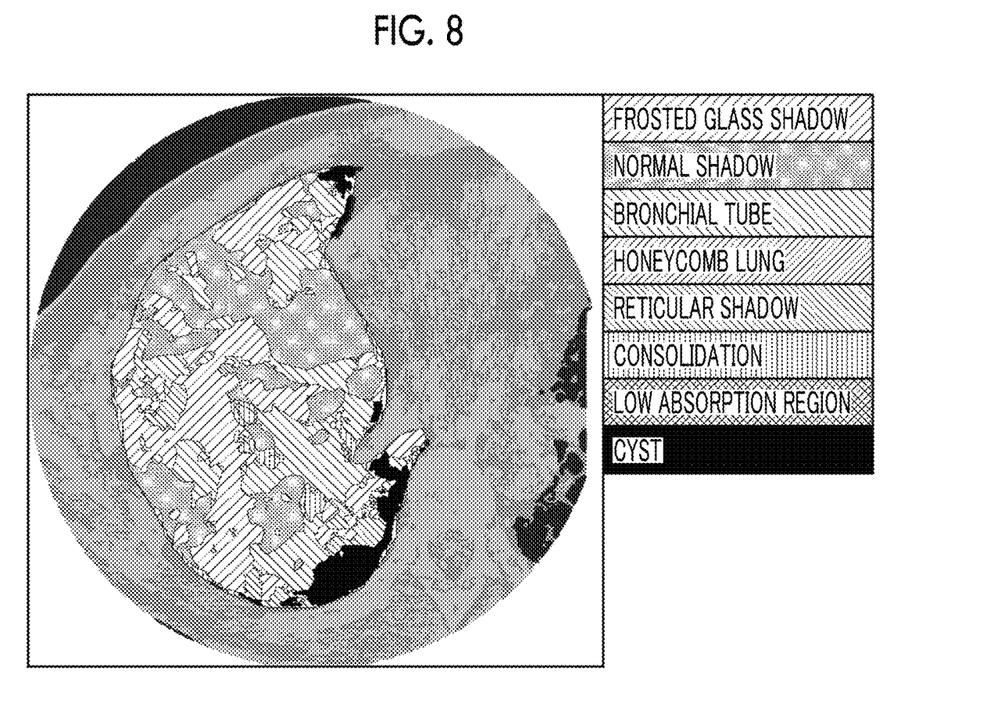
FIG. 8 is a diagram showing an example of a mapping image.

Specifically, the display controller 15 allocates the same color with respect to pixels that belong to the same classification, with respect to every pixel on a three-dimensional space classified into any one of the above-described eight types of tissues or lesions, to generate a three-dimensional mapping image. FIG. 8 is a diagram showing an example of a mapping image in which a color based on each classification is allocated to each of the eight types of classifications. In FIG. 8, a sectional image of an arbitrary section in a three-dimensional mapping image is shown, but the invention is not limited thereto, and the three-dimensional mapping image may be displayed on the display device 20.

Further, the display controller 15 is capable of displaying sectional images in a plurality of sectional directions acquired by the sectional image acquisition unit 11, sectional images that are subjected to the primary classification process in the primary classification unit 12, and sectional images that are subjected to the secondary classification process in the secondary classification unit 13 or a three-dimensional image on the display device 20.

The display device 20 includes, for example, a liquid crystal display, or the like. Further, the display device 20 may be configured of a touch panel, and may be commonly used as the input device 30.

The input device 30 includes a mouse, a keyboard, or the like, and receives various setting inputs from a user. Specifically, for example, the input device 30 receives a setting input of identification information on a patient, or the like.

Figure 9:
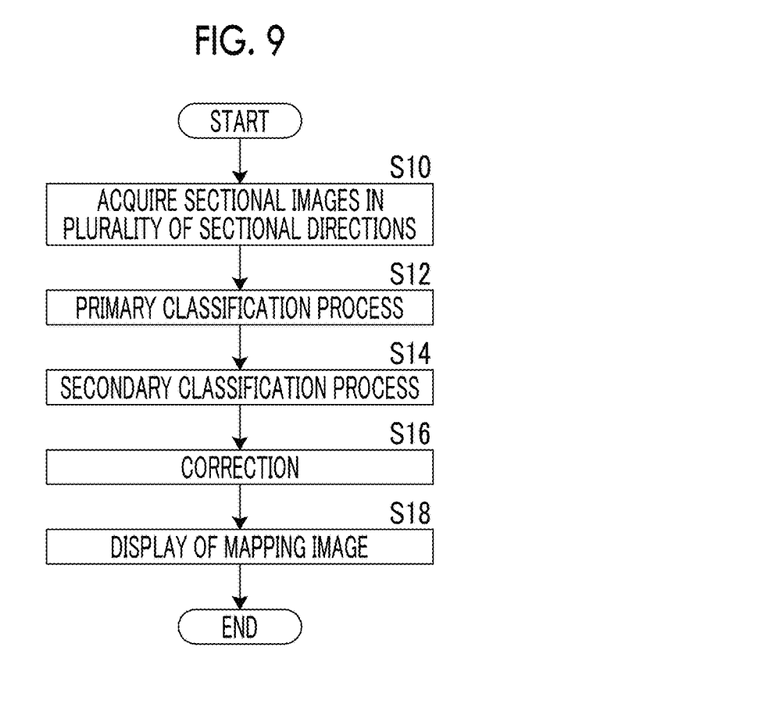
FIG. 9 is a flowchart for illustrating an operation of a medical image diagnosis support system using an embodiment of an image processing apparatus according to the invention.

Next, an operation of a medical image diagnosis support system according to this embodiment will be described with reference to a flowchart shown in FIG. 9.

First, sectional images in a plurality of sectional directions of a patient are acquired according to a setting input of identification information on the patient or the like from a user (S10).

The plurality of sectional images are output to the primary classification unit 12, and the primary classification unit 12 performs a primary classification process with respect to each of the input sectional images to specify the type of a tissue or a lesion to which each pixel of each sectional image belongs (S12).

Further, a result of the primary classification process in the primary classification unit 12 is output to the secondary classification unit 13, and the secondary classification unit 13 performs a secondary classification process on the basis of the input result of the primary classification process (S14). Specifically, the secondary classification unit 13 evaluates the result of the primary classification process with respect to each sectional image, with respect to a pixel that is common to the sectional images in the plurality of sectional directions, the type of a tissue or a lesion to which the pixel belongs is re-specified.

In addition, a result of the secondary classification process in the secondary classification unit 13 is output to the correction unit 14, and the correction unit 14 corrects the input result of the primary classification process (S16).

Furthermore, the result of the secondary classification process corrected by the correction unit 14 is output to the display controller 15, and the display controller 15 allocates colors to respective classified regions to generate a mapping image, and displays the mapping image on the display device 20 (S18).

According to the medical image diagnosis support system according to the above-described embodiment, a primary classification process of acquiring sectional images in a plurality of different sectional directions of a test subject and specifying the type of a tissue or a lesion to which each pixel of each sectional image belongs, with respect to each of the plurality of sectional images, is performed. Then, a secondary classification process of evaluating a result of the primary classification process with respect to each sectional image, with respect to a pixel that is common to the plurality of sectional images, to re-specify the type of a tissue or a lesion to which the pixel that is common to the plurality of sectional images belongs, is performed. By performing the secondary classification process in this way, it is possible to obtain a classification result in further consideration of a depth direction of sectional images.

Further, since the result of the secondary classification process is corrected on the basis of an anatomic feature of a tissue or a lesion, or an image feature value thereof, it is possible to achieve a classification result based on an anatomic structure, and to classify a region of the tissue or the lesion with high accuracy.

What is claimed is:

1. An image processing apparatus comprising:
    a sectional image acquisition unit that acquires a plurality of sectional images in a plurality of different sectional directions of a test subject;
    a primary classification unit that performs a primary classification process of specifying, with respect to each of the plurality of sectional images, the type of a tissue or a lesion to which each pixel of each sectional image belongs;
    a secondary classification unit that performs a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs; and
    a correction unit that corrects a result of the secondary classification process on the basis of an anatomic feature of the tissue or the lesion, or an image feature value thereof.

2. The image processing apparatus according to claim 1, wherein the correction unit corrects the result of the secondary classification process with respect to each pixel using a sectional image in a specific sectional direction.

3. The image processing apparatus according to claim 2, wherein the specific sectional direction is a slicing direction in imaging of the test subject.

4. The image processing apparatus according to claim 2, wherein the sectional image in the specific sectional direction is a sectional image with the highest resolution among the sectional images in the plurality of sectional directions.

5. The image processing apparatus according to claim 2, wherein the correction unit corrects the result of the secondary classification process on the basis of a signal value of each pixel of the sectional image in the specific sectional direction.

6. The image processing apparatus according to claim 1, wherein the correction unit corrects the result of the secondary classification process on the basis of an anatomic feature of the shape or the position of the tissue or the lesion.

7. The image processing apparatus according to claim 1, wherein the correction unit corrects, in a case where there is an abnormality in continuity in a three-dimensional space of an edge or a centroid position of a tissue or a lesion specified by each pixel classified by the secondary classification process, the result of the secondary classification process with respect to each pixel.

8. The image processing apparatus according to claim 1, wherein in a case where the secondary classification unit performs the second classification process, the secondary classification unit adds a weight based on each resolution of each of the sectional images to the result of the primary classification process with respect to each sectional image for the evaluation.

9. The image processing apparatus according to claim 1, wherein the primary classification unit performs the primary classification process using a discriminator generated through machine learning.

10. An image processing method comprising:
acquiring a plurality of sectional images in a plurality of different sectional directions of a test subject;
performing a primary classification process of specifying, with respect to each of the plurality of sectional images, the type of a tissue or a lesion to which each pixel of each sectional image belongs;
performing a secondary classification process of evaluating results of the primary classification process with respect to of the plurality of each sectional images, with respect to a pixel that is common to the plurality of sectional images, to re-specify the type of a tissue or a lesion to which the pixel that is common to the plurality of sectional images belongs; and
correcting a result of the secondary classification process on the basis of an anatomic feature of the tissue or the lesion, or an image feature value thereof.

11. A non-transitory computer-readable storage medium storing therein an image processing program that causes a computer to function as:

a sectional image acquisition unit that acquires a plurality of sectional images in a plurality of different sectional directions of a test subject;

a primary classification unit that performs a primary classification process of specifying, with respect to each of the plurality of sectional images, the type of a tissue or a lesion to which each pixel of each sectional image belongs;

a secondary classification unit that performs a secondary classification process of evaluating results of the primary classification process with respect to each of the plurality of sectional images, with respect to a pixel that is common to the plurality of sectional images, to re-specify the type of a tissue or a lesion to which the pixel that is common to the plurality of sectional images belongs; and a correction unit that corrects a result of the secondary classification process on the basis of an anatomic feature of the tissue or the lesion, or an image feature value thereof.

* * * * *